United States Patent [10] Patent No.: US 8,518,213 B2
Retsina et al. (45) Date of Patent: Aug. 27, 2013

(54) PROCESS FOR PRODUCING ALCOHOL AND OTHER BIOPRODUCTS FROM BIOMASS EXTRACTS IN A KRAFT PULP MILL

(75) Inventors: Theodora Retsina, Atlanta, GA (US); Vesa Pylkkanen, Atlanta, GA (US)

(73) Assignee: API Intellectual Property Holdings, LLC, Atlanta, GA (US)

( * ) Notice: Subject to any disclaimer, the term of this patent is extended or adjusted under 35 U.S.C. 154(b) by 0 days.

(21) Appl. No.: 13/500,917

(22) PCT Filed: Oct. 7, 2010

(86) PCT No.: PCT/US2010/051759
§ 371 (c)(1),
(2), (4) Date: Apr. 9, 2012

(87) PCT Pub. No.: WO2011/044320
PCT Pub. Date: Apr. 14, 2011

(65) Prior Publication Data
US 2012/0208250 A1 Aug. 16, 2012

Related U.S. Application Data

(60) Provisional application No. 61/250,050, filed on Oct. 9, 2009.

(51) Int. Cl.
*D21C 11/00* (2006.01)
(52) U.S. Cl.
USPC .......... 162/19; 162/65; 162/82; 435/136
(58) Field of Classification Search
None
See application file for complete search history.

(56) References Cited

PUBLICATIONS

Huang et al. "Process modeling and analysis of pulp mill-based integrated biorefinery with hemicellulose pre-extraction for ethanol production: a comparative study" (2009) Bioresource Technology, vol. 101: 624-631.*

* cited by examiner

*Primary Examiner* — Jon P Weber
*Assistant Examiner* — Teresa E Knight
(74) *Attorney, Agent, or Firm* — Ryan P. O'Connor

(57) ABSTRACT

A method for the production of alcohol and other bioproducts from power boiler woody biomass extract containing hemicelluloses, with or without combining extract from wood prior to Kraft cooking. The process is integrated with the host Kraft pulp mill plant process to minimize the heat loss from extracting hemicelluloses and the energy used in the process.

16 Claims, 2 Drawing Sheets

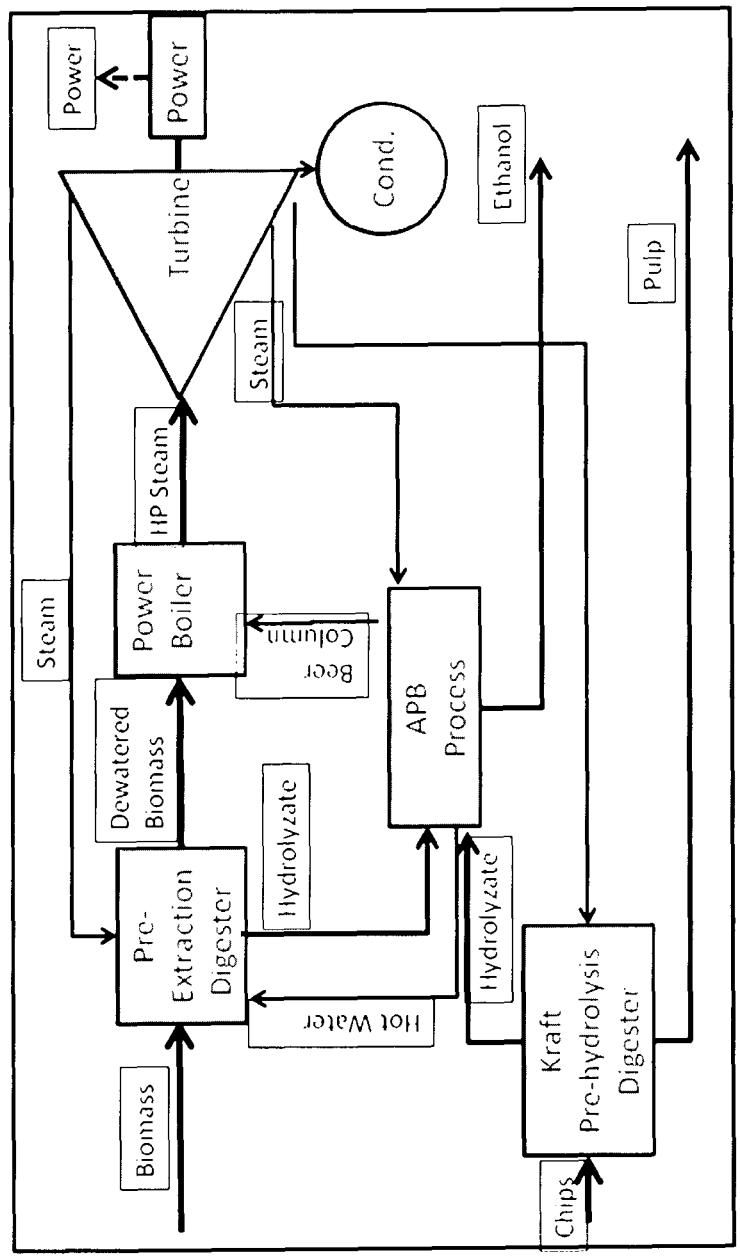
Figure 1. An overall flow sheet example of the invention process.

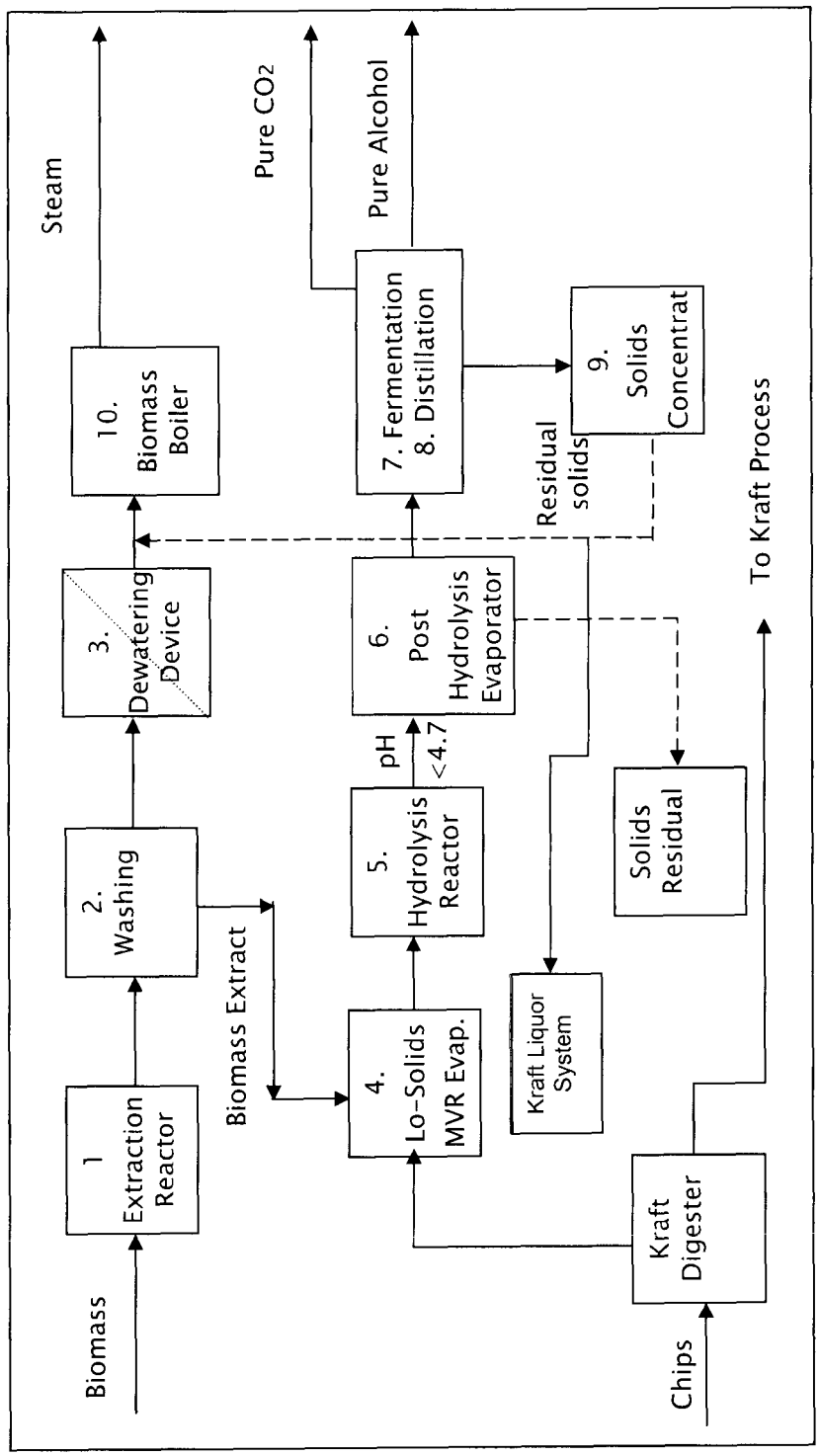
Figure 2. A detailed flow sheet example of the invention process. Process steps may be in other sequences.

PROCESS FOR PRODUCING ALCOHOL AND OTHER BIOPRODUCTS FROM BIOMASS EXTRACTS IN A KRAFT PULP MILL

FIELD OF THE INVENTION

This invention relates, in general, to the process extracting and treating of extracts of biomass prior to a biomass boiler, potentially combined with extract from biomass prior to Kraft process, and treatment of this extract for production of alcohol and other bioproducts in a Kraft pulp mill.

BRIEF DESCRIPTION OF THE DRAWINGS

A more complete understanding of the present invention may be obtained by reference to the following detailed description when read in conjunction with the accompanying drawings wherein:

FIG. 1. illustrates a conceptual flow sheet example of the invention process.

FIG. 2. illustrates a typical general arrangement of the unit operations for mixed biomass derived extract by steam explosion prior to a power plant combustor.

BACKGROUND OF THE INVENTION

Renewable power generation from forest residues is commonly practiced in the forest products industries. The U.S. forest products industry consumed 27.1 million tons of wood derived biomass, called "hog fuel", in the generation of steam. By comparison, the power generation industry used 11.9 million tons of biomass of which 80% is wood derived. The biomass consumption in power generation is expected to double in every 10 years until 2030.

The major wood components are lignin, hemicelluloses and cellulose. The steam explosion process dissolves predominantly hemicelluloses in temperatures above 160° C. Hemicelluloses fraction removed in this process is termed "extract". A concentration of the extract through evaporation is energy intensive, although it is currently practiced to produce molasses.

Previous research indicates that ethanol, acetic acid and their byproducts can be derived from the wood extract. Especially hardwood produces an extract rich in acetic acid and sugars as taught by Amidon et al. in (U.S. Patent Application No. 2007/0079944 A1, Apr. 12, 2007).

The current inventors, Retsina; et al.(U.S. Patent Filing No. 61/175,588) have previously described a steam extraction and hydrolysis process, in which an alkaline acetate product is concentrated in reverse osmosis membrane from evaporator condensate. The clean permeate is further recycled to the host mill to achieve zero effluent operation. Furthermore, the current inventors Retsina; et al. (U.S. Patent Application No. 61/219,764) have described the process integration of the waste heat to temper power boiler feed water.

The current inventors found an alternative method to produce fermented alcohol, ethanol or butanol, from biomass extraction using steam explosion, followed by vapor recompression evaporation, acid hydrolysis, fermentation and distillation. The present inventors have now developed a process, wherein the hemicelluloses in the power plant biomass extract can be converted to chemical products in an energy efficient process.

SUMMARY OF THE INVENTION

The present invention describes a process for the production of alcohol and other bioproducts from power boiler biomass extract, combined or not, with extract from the pretreatment of wood chips prior to Kraft process digestion. Treatment of hemicelluloses in the extract through hydrolysis, evaporation, fermentation and distillation steps is used to recover and concentrate alcohol and acetate products. The process is integrated with the host plant to reuse water and to minimize process energy and water consumption.

DETAILED DESCRIPTION OF THE INVENTION

The first step of the process is biomass extraction. Woody biomass is charged in a batch or continuous reactor vessel along with steam and heated to between 5 and 30 atmospheres pressure for 2 or more minutes to obtain 10-30% of wood as dissolved solids. In one manifestation, this extract is combined with extract from the Kraft mill digester. In the Kraft mill digester, a first stage of steam extraction is practiced prior to the Kraft cooking.

The second step of the process is washing of biomass. The heated biomass is washed with hot water or condensate and drained to recover dissolved wood components. The wash filtrate contains dissolved xylan, glucan, mannan, arbinan, galactan and acetyl groups in oligomers of hemicelluloses as well as lignin. The wash filtrate has low organic solids concentration in between 1% and 15%. The majority of the water must be removed before an economic treatment of hemicelluloses is possible.

The third step of the process is compaction of the biomass. The remaining solid biomass is subjected to mechanical pressure through a plug screw feeder. This compaction dewaters the biomass to uniform moisture of 60% or less, which is similar to delivered biomass from the forest.

The fourth step of the process is low solids evaporation. Evaporation of the wash filtrate or extract using mechanical vapor recompression is suitable for low solids concentration up to around 25%, because the boiling point rise is small. Evaporated vapor is compressed and condensed in the hot side of the evaporator to produce more evaporation. If the wash filtrate or extract feed concentration is over 5%, this step may be omitted. When the pH is kept below acetic acid dissociation point at 4.8, acetic acid, a fermentation inhibitor, is volatilized to vapor fraction.

The fifth step of the process is hydrolysis. Sulfuric acid or enzymes can be used to hydrolyze the sugars, which were concentrated in the low solids evaporator. Oligomeric hemicelluloses are converted into monomer sugars and acetyl groups are released. The hydrolyzate pH is controlled following the hydrolysis to maintain acetic acid in the unassociated form. Hydrolysis can be performed in batch or continuous mode. As an option at the end of this step, the pH may be adjusted with lime or another chemical and any precipitated solids may be washed and treated separately.

The sixth step of the process is post hydrolysis evaporation. Evaporation using mechanical vapor recompression is performed to concentrate the hydrolyzate to 15%-35% solids. More of the remaining acetic acid and water is evaporated in this step. Under the appropriate economic criteria, this step could be done with steam evaporation.

The seventh step of the process is fermentation of wood sugars. The sugars in the evaporated hydrolyzate are fermented in continuous or batch tanks with one or more microorganisms capable of converting five and six-carbon sugars into alcohol and carbon dioxide. The majority of acetic acid, which may inhibit fermentation, was removed in the previous evaporation step. Some additional acetic acid may be formed in the fermentation steps. Nutrients and pH adjustment chemicals, as well as make-up fermentative organism, are added in the fermentors as and if needed. Carbon dioxide is removed from the fermentors and scrubbed with cool water for alcohol recovery. This purified gas can be further compressed and sold as industrial grade carbon dioxide. The fermentation broth, commonly termed "beer", from the fermentation step is sent to a distillation column.

The eighth step of the process is distillation of alcohol. The beer from the fermentation processes is sent to a distillation column to separate the alcohol from the solids and residual sugars. Alcohol leaving as the overhead from the distillation column is recovered at approximately 50 mass-% strength. The final concentration of the alcohol product is performed in a rectifying column and molecular sieve to obtain over 99-mass % alcohol. In one manifestation, the beer column is integrated in the existing Kraft mill multiple-effect evaporator train so that it runs as an effect and avails itself of the multiple effect economy of the Kraft evaporator.

The ninth step of the process is the solids concentration from the stillage. The solids, commonly termed stillage, from the distillation beer column bottom can be further evaporated in an optional mechanical vapor concentrator to achieve zero-liquid discharge operation. The concentrated sludge can be burned in a biomass boiler to increase steam generation. Alternatively, this concentration can happen by injecting the distillation bottoms in the weak black liquor of the existing Kraft mill, so that it is evaporated using multiple-effect economy in the existing Kraft evaporator.

The tenth step of the process is combustion of biomass. The compacted biomass from the third step and concentrated solids from the ninth step are fed to a traditional biomass combustion unit. The heat of combustion is used to raise steam, which drives a steam turbine to generate electricity, or the steam can be used for the process.

In one manifestation of the invention, hydrolysis and fermentation (the seventh and tenth steps) may be combined in one step by using a third party proprietary microorganism.

The invention claimed is:

1. A process for the production of alcohol, power, and pulp from biomass, said process comprising:
   (a) extracting a first biomass feedstock with steam or hot water, to generate a first liquid hydrolyzate and a first extracted-solids stream;
   (b) extracting a second biomass feedstock, in the form of wood chips, with steam in a Kraft digester, to generate a second liquid hydrolyzate and a second extracted-solids stream;
   (c) combining said first liquid hydrolyzate and said second liquid hydrolyzate to generate a combined hydrolyzate;
   (d) further hydrolyzing said combined hydrolyzate with an acid or enzymes to convert oligomeric hemicelluloses into monomer sugars;
   (e) fermenting said monomer sugars to produce an alcohol;
   (f) combusting said first extracted-solids stream to produce power; and
   (g) pulping said second extracted-solids stream to produce pulp.

2. The process of claim 1, wherein said first biomass feedstock and said second biomass feedstock are both wood feedstocks.

3. The process of claim 1, said process further comprising dewatering said first extracted-solids stream to generate dewatered solids having 60 wt % or less water.

4. The process of claim 1, said process further comprising evaporating said combined hydrolyzate prior to step (d), using mechanical-vapor recompression evaporation.

5. The process of claim 4, wherein said combined hydrolyzate is maintained at a pH below 4.8 to volatilize acetic acid during said evaporating.

6. The process of claim 1, said process further comprising evaporating said combined hydrolyzate after step (d) and prior to step (e), using mechanical-vapor recompression evaporation.

7. The process of claim 6, wherein said combined hydrolyzate is maintained at a pH below 4.7 to volatilize acetic acid during said evaporating.

8. The process of claim 7, said process further comprising recovering an acetate product derived from said acetic acid.

9. The process of claim 1, wherein said alcohol is ethanol.

10. The process of claim 1, wherein said alcohol is butanol.

11. The process of claim 1, wherein production and purification of said alcohol is integrated with a host Kraft pulp mill that includes said Kraft digester, to minimize heat loss and energy use.

12. The process of claim 1, wherein a separate multiple-effect evaporator is integrated with an alcohol distillation column for purifying said alcohol.

13. The process of claim 12, wherein said multiple-effect evaporator is located at a host Kraft pulp mill that includes said Kraft digester.

14. The process of claim 12, said process further comprising injecting distillation column bottoms into weak black liquor of a Kraft pulp mill that includes said Kraft digester, to concentrate said distillation column bottoms.

15. The process of claim 1, said process further comprising combining concentrated distillation column bottoms with said first extracted-solids stream prior to said combusting.

16. The process of claim 1, wherein step (f) produces high-pressure steam suitable for a turbine to generate said power, and wherein used steam from step (f) is recycled to step (b) and/or step (d).

* * * * *